(12) United States Patent
Zaiki et al.

(10) Patent No.: US 9,084,581 B2
(45) Date of Patent: Jul. 21, 2015

(54) X-RAY IMAGING SYSTEM

(75) Inventors: Ryuji Zaiki, Utsunomiya (JP); Teruomi Gunji, Otawara (JP); Katsuie Ikawa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 384 days.

(21) Appl. No.: 13/522,046

(22) PCT Filed: Dec. 5, 2011

(86) PCT No.: PCT/JP2011/078062
§ 371 (c)(1), (2), (4) Date: Jul. 13, 2012

(87) PCT Pub. No.: WO2012/081436
PCT Pub. Date: Jun. 21, 2012

(65) Prior Publication Data
US 2013/0051522 A1    Feb. 28, 2013

(30) Foreign Application Priority Data

Dec. 16, 2010  (JP) .................................. 2010 280062

(51) Int. Cl.
*H05G 1/02* (2006.01)
*A61B 6/00* (2006.01)
*A61B 6/04* (2006.01)

(52) U.S. Cl.
CPC ............... *A61B 6/547* (2013.01); *A61B 6/0407* (2013.01)

(58) Field of Classification Search
CPC ........ A61B 6/032; A61B 6/04; A61B 6/4441; A61B 6/466
USPC ................................... 378/195–198, 208, 209
See application file for complete search history.

(56) References Cited

U.S. PATENT DOCUMENTS

2002/0090058 A1    7/2002  Yasuda et al.
2008/0260103 A1*  10/2008  Zaiki ............................ 378/150
(Continued)

FOREIGN PATENT DOCUMENTS

JP    08-238232    9/1996
JP    8 308821    11/1996
(Continued)

OTHER PUBLICATIONS

International Search Report Issued Feb. 21, 2012 in PCT/JP11/78062 Filed Dec. 5, 2011.
(Continued)

*Primary Examiner* — Michael Maskell
(74) *Attorney, Agent, or Firm* — Oblon, McClelland, Maier & Neustadt, L.L.P.

(57) ABSTRACT

An X-ray imaging system that allows X-ray images to be acquired from a desired direction by considering the tilt of a tabletop. The X-ray imaging system includes a support unit that holds an X-ray imaging unit that performs X-ray imaging of a subject. The subject is placed on the tabletop. A memory stores in advance imaging angle information from previous imaging. A tilt detector detects the tilt angle of the tabletop. A calculator calculates a correction angle for correcting the imaging angle information based on the imaging angle information and on the tilt angle. A drive unit moves the support unit to a position based on the imaging angle information and the correction angle.

5 Claims, 13 Drawing Sheets

(56) References Cited

U.S. PATENT DOCUMENTS

2009/0003518 A1 1/2009 Sadakane et al.
2009/0207965 A1* 8/2009 Sakaguchi .................. 378/4

FOREIGN PATENT DOCUMENTS

| JP | 2001 78964 | 3/2001 |
|----|------------|--------|
| JP | 2001 292984 | 10/2001 |
| JP | 2002 186605 | 7/2002 |
| JP | 2003-210447 A | 7/2003 |
| JP | 2004 121604 | 4/2004 |
| JP | 2005-185565 | 7/2005 |
| JP | 2006 25893 | 2/2006 |
| JP | 2006 314704 | 11/2006 |
| JP | 2008 148925 | 7/2008 |
| JP | 2009 5984 | 1/2009 |

OTHER PUBLICATIONS

Combined Chinese Office Action and Search Report issued Apr. 1, 2013 in Patent Application No. 201180010627.X.
Office Action issued May 12, 2015, in Japanese Patent Application No. 2010-280062, filed Dec. 16, 2010.

* cited by examiner

X-RAY IMAGING SYSTEM

FIELD

Embodiments of the present invention relate to an X-ray imaging system.

BACKGROUND

An X-ray imaging system is a system that radiates X-rays for a subject placed on a tabletop, detects X-rays that have transmitted the subject, and composes images showing the detected distribution of X-ray intensity.

In an X-ray imaging system, an operation to tilt the tabletop may be performed to image the subject from various angles.

For example, in IVR (Interventional Radiology), a therapeutic manipulation (hybrid manipulation) by which a catheter manipulation and surgical treatment are implemented in parallel may be used. In this manipulation, the tabletop is often tilted to allow the operator to conduct the treatment more easily.

Moreover, X-ray imaging systems have auto-positioning and auto-angle functions.

Auto-positioning is a function whereby multiple arbitrary positions of a support unit, etc. that holds an X-ray tube, etc. are linked with arbitrary numbers and stored in advance, and when an operator inputs a desired number during an examination, the support unit, etc. is automatically arranged at the position linked to that number. Auto-angle is a function that reproduces angles of the support unit based on supplementary information (imaging angle information) of images collected in the past.

By executing these functions, it is possible to adjust the angle of the support unit in relation to the subject to a predetermined value.

PRIOR ART DOCUMENTS

Patent Documents

[Patent Document 1] Japanese published unexamined application 2004-121604

SUMMARY OF THE INVENTION

Problems to be Resolved by the Invention

Conventionally, when auto-positioning and/or auto-angle are executed, even if the tabletop is in a tilted state, the support unit, etc. is moved without considering the tilt angle. Consequently, it is not possible to arrange the support unit at the position desired by the operator (i.e., the position is misaligned due to the tilt angle of the tabletop), and it is not possible to acquire X-ray images from a desired direction.

The embodiments describe an X-ray imaging system that, in order to resolve the above problems, can acquire X-ray images from a desired direction by considering the tilt of the tabletop.

Means of Solving the Problems

To solve the above problems, the X-ray imaging system described in the embodiments includes a support unit that holds an X-ray imaging unit that performs X-ray imaging of a subject. The subject is placed on a tabletop. A memory stores in advance imaging angle information from past imaging. A tilt detector detects the tilt angle of the tabletop. A calculator calculates a correction angle for correcting the imaging angle information based on the imaging angle information and on the tilt angle. A drive unit moves the support unit to a position based on the imaging angle information and the correction angle.

MODES FOR CARRYING OUT THE INVENTION

First Embodiment

The configuration of an X-ray imaging system 1 according to the first embodiment will be described with reference to FIG. 1 through FIG. 4D.

<Device Configuration>

Figure 1:
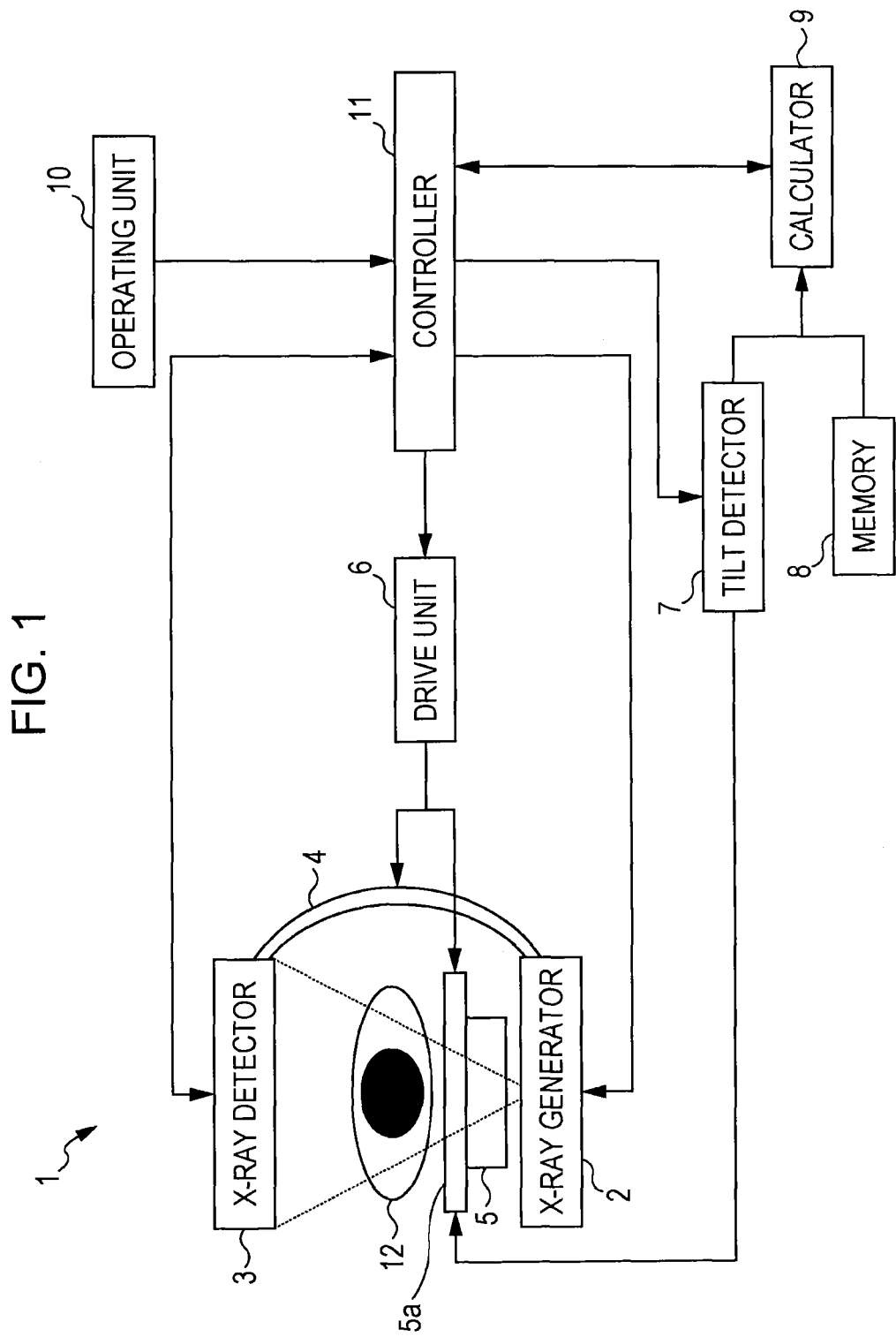
FIG. 1 is a block diagram showing the configuration of the X-ray imaging system according to the first embodiment.

As shown in FIG. 1, the X-ray imaging system 1 includes an X-ray generator 2, an X-ray detector 3, a support unit 4, a couch 5, a drive unit 6, a tilt detector 7, a memory 8, a calculator 9, an operating unit 10, and a controller 11. During X-ray imaging, a subject 12 is arranged between the X-ray generator 2 and the X-ray detector 3.

The X-ray generator 2 has a function to generate X-rays and irradiate X-rays to the region of the subject 12 being examined. The X-ray generator 2 includes an X-ray tube (not shown), etc. that generates X-rays when a voltage is applied by a high-voltage generator that generates high voltages.

The X-ray detector 3 has a function to detect X-rays that have been irradiated from the X-ray generator 2 to the subject 12 and have transmitted the subject 12. The detected X-rays are converted into X-ray image information by the X-ray detector 3, for example. The X-ray image information is transmitted to the memory 8 via wiring, etc. (not shown) and stored.

The support unit 4 holds the X-ray generator 2 and the X-ray detector 3. The support unit 4 has, for example, a shape like types of character C that is known as a C-arm. The support unit 4 is able to move in the vicinity of the couch 5 due to the drive unit 6. The X-ray generator 2 and the X-ray detector 3 are provided at mutually facing positions by being held by the support unit 4. Consequently, it is possible to arrange the subject 12 between the X-ray generator 2 and the X-ray detector 3.

In the present embodiment, the X-ray generator 2 and the X-ray detector 3 configure the "X-ray imaging unit". In other words, the support unit 4 holds the X-ray imaging unit.

The couch 5 includes a movable tabletop 5a. On the tabletop 5a, the subject 12 that is the subject of X-ray imaging is placed. The tabletop 5a is moved and tilted by the drive unit 6.

Figure 2A:
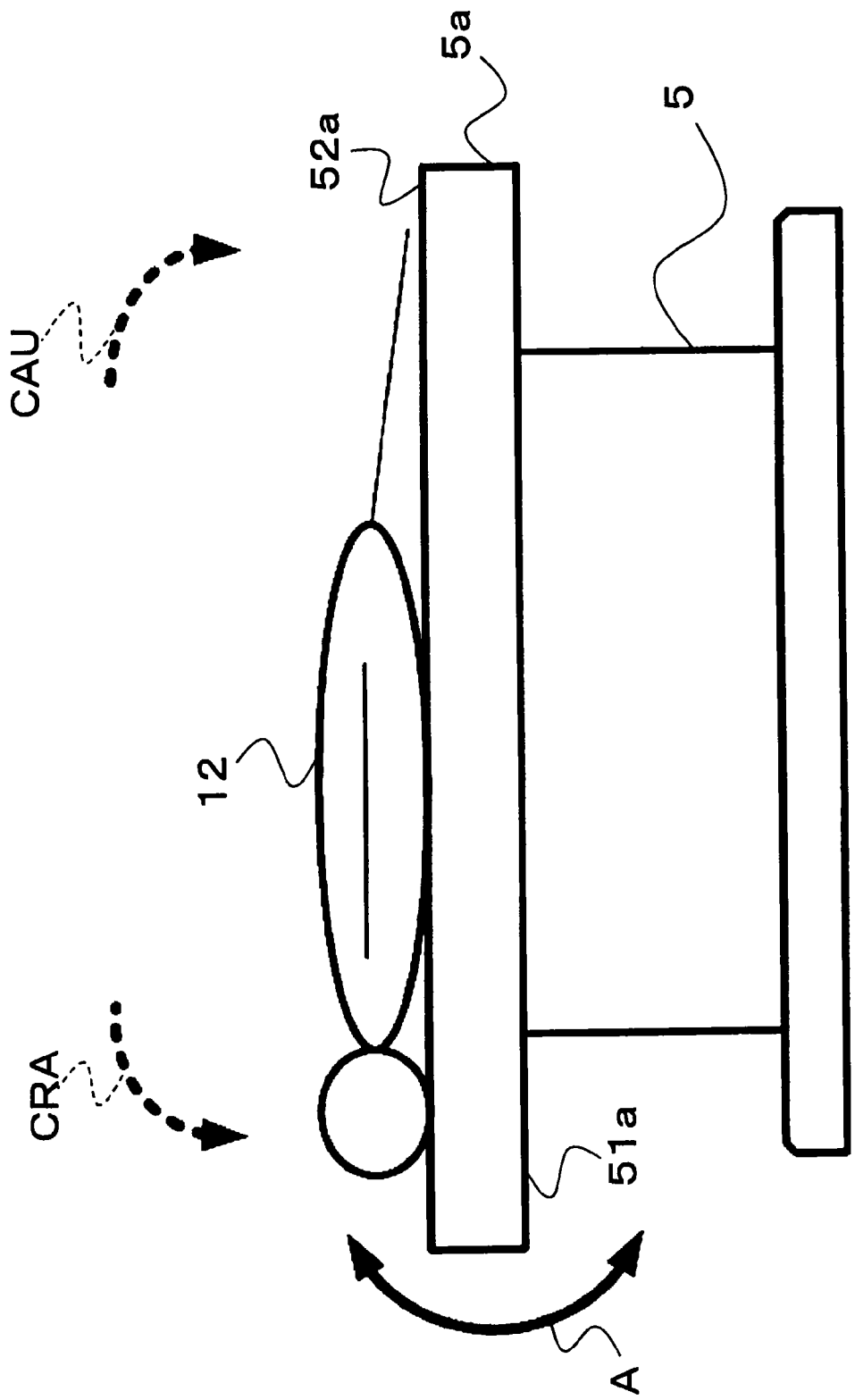
FIG. 2A is a diagram showing additional details of the configuration of the X-ray imaging system according to the first embodiment.
Figure 2B:
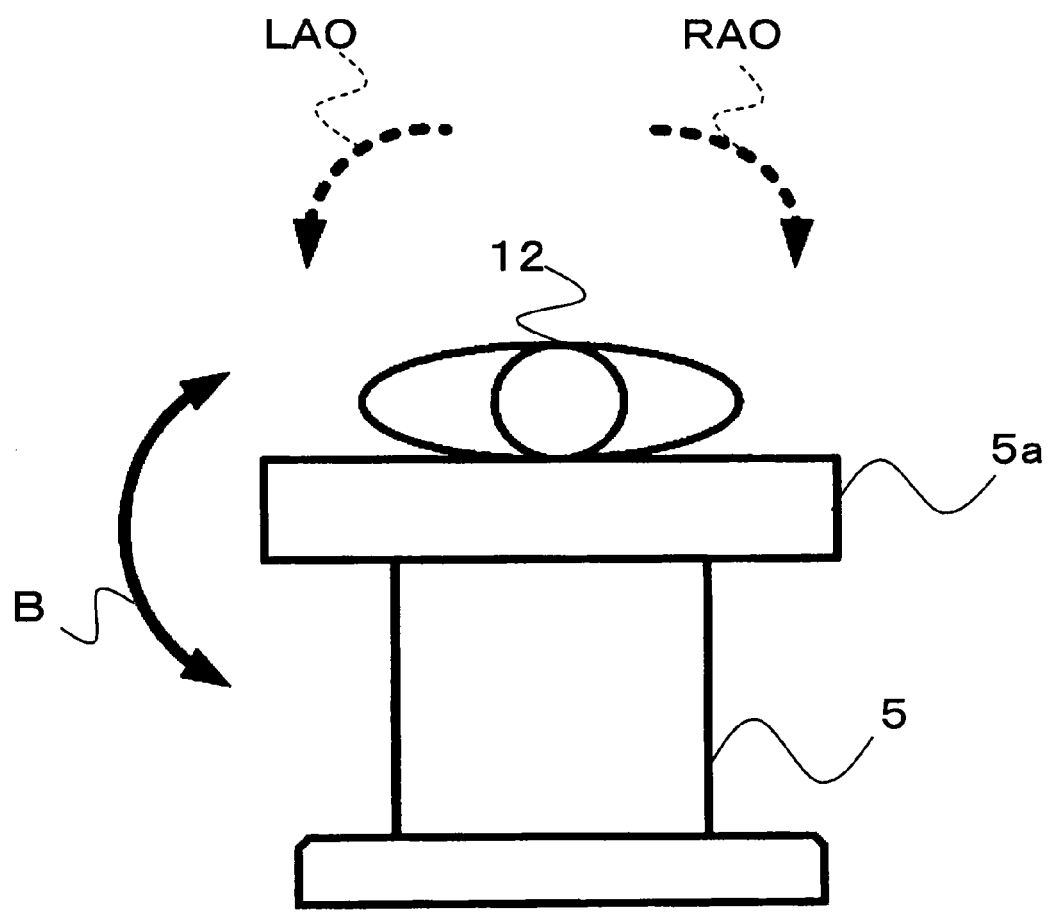
FIG. 2B is a diagram showing additional details of the configuration of the X-ray imaging system according to the first embodiment.

As shown in FIG. 2A and FIG. 2B, in the present embodiment, "tilting" the tabletop 5a refers to tilting the tabletop 5a up and down in the longitudinal direction (in the direction of arrow A in FIG. 2A) or to tilting the tabletop 5a up and down in the lateral direction (in the direction of arrow B in FIG. 2B).

Moreover, in the present embodiment, the subject 12 is placed along the longitudinal direction of the tabletop 5a. The tabletop 5a has an anterior part 51a, where the head side of the subject 12 is arranged, and a posterior part 52a, where the feet side is arranged. Moreover, as shown in FIG. 2A, "CRA" (Cranial) refers to the rotational direction toward the anterior part 51a when the lateral direction is used as the axis. "CAU" (Caudal) refers to the rotational direction toward the posterior part 52a when the lateral direction of the tabletop 5a is used as the axis. Moreover, as shown in FIG. 2B, "LAO" (Left Anterior Oblique) refers to the rotational direction toward the left (leftward on the page) when the longitudinal direction of the tabletop 5a is used as the axis. "RAO" (Right Anterior Oblique) refers to the rotational direction toward the right (rightward on the page) when the longitudinal direction of the tabletop 5a is used as the axis.

The drive unit 6 has a function to move the support unit 4 and the tabletop 5a. The drive unit 6 is able to drive the support unit 4 and the tabletop 5a separately. In other words, the drive unit 6 is able to drive both the support unit 4 and the tabletop 5a simultaneously, and is also able to drive either the support unit 4 or the tabletop 5a (both the support unit 4 and the tabletop 5a).

The tilt detector 7 has a function to detect the tilt angle of the tabletop 5a. The detection of the tilt angle is performed by, for example, fixing a predetermined coordinate axis in advance and detecting the degree by which the tabletop 5a is tilted in relation to the coordinate axis. Moreover, the tilt angle may be detected based on control signals sent from the controller 11 to the drive unit 6.

The detection of the tilt angle by the tilt detector 7 is executed when, based on an input from the operating unit 10, for example, the controller 11 starts operation control of the tilt detector 7.

The memory 8 has a function to store imaging angle information at the time of past imaging as well as detection results, etc. from the X-ray detector 3. The term "imaging angle information (at the time of past imaging)" as used herein refers to information indicating the tilt angle of a device used to perform imaging.

The imaging angle information in the present embodiment is information (position information; hereinafter also referred to as "auto-positioning information") that is linked to an arbitrary identifier and indicates a position of the support unit 4. The identifier is, for example, a number (No. 1, No. 2, etc.). By using numbers as identifiers in this manner, it becomes possible to sequence and identify various positions of the support unit 4.

The calculator 9 has a function to calculate a correction angle for correcting the imaging angle information based on the imaging angle information at the time of past imaging stored in the memory 8, as well as on the tilt angle detected by the tilt detector 7. In the present embodiment, by coupling the tilt angle detected by the tilt detector 7 with the auto-positioning information of the support unit 4, a correction angle for correcting the auto-positioning information of the support unit 4 is calculated. The term "correction angle" as used herein refers to a value used to adjust the imaging angle information stored in the memory 8.

The operating unit 10 is used to input details of instruction for various operations of the X-ray imaging system 1, such as inputs of instructions for the start and stopping of X-ray imaging performed by the X-ray imaging unit, or inputs of instructions to move the support unit 4 and/or the tabletop 5a. Therefore, it is possible to cause the X-ray imaging system 1 to execute desired operations. Moreover, the operating unit 10 may include a separate input means, such as a mouse or a keyboard.

The controller 11 has a function to control the operations of the various configurations of the X-ray imaging system 1, such as the X-ray generator 2, the X-ray detector 3, the drive unit 6, and the tilt detector 7. The controller 11 is able to start and stop the control of each configuration based on inputs, etc. from the operating unit 10. The controller 11 performs operational control of each configuration based on, for example, programs stored in the memory 8. Moreover, in the present embodiment, the controller 11 executes predetermined processing operations (described later) based on programs.

<Operations of the X-Ray Imaging System 1>

Figure 3:
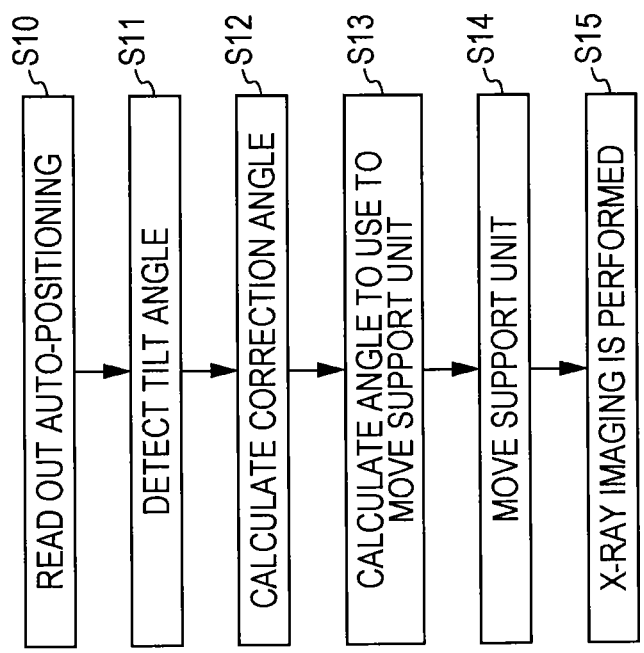
FIG. 3 is a flowchart showing an overview of processes performed by the X-ray imaging system according to the first embodiment.
Figure 4A:
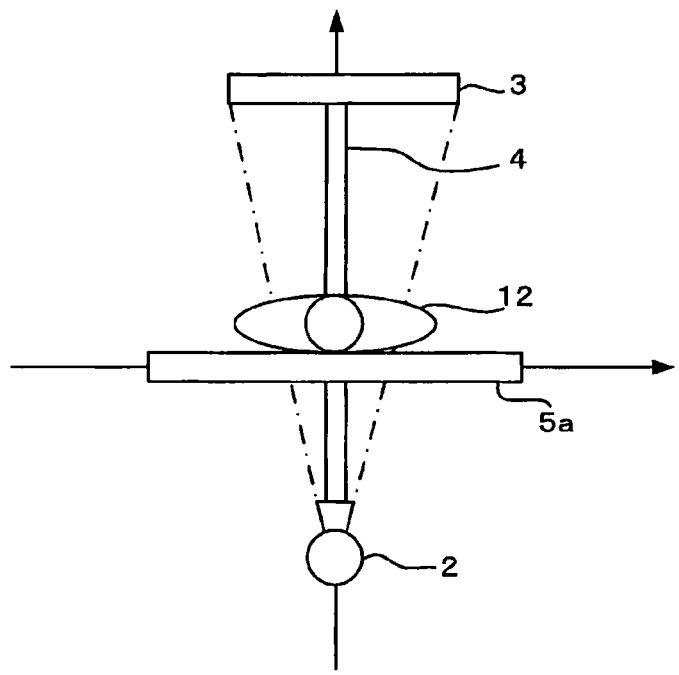
FIG. 4A is a diagram supplementing the descriptions of the flowchart according to the first embodiment.
Figure 4B:
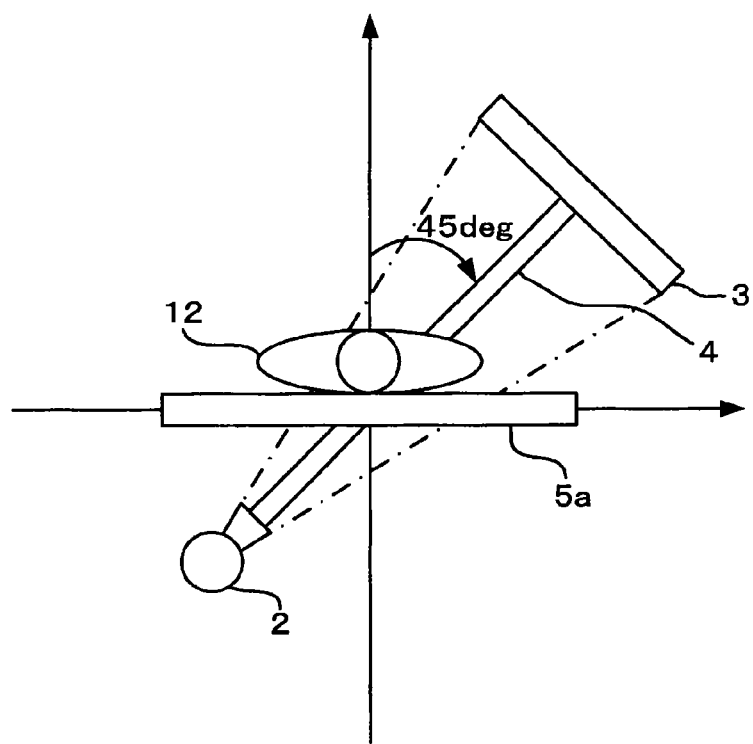
FIG. 4B is a diagram supplementing the descriptions of the flowchart according to the first embodiment.
Figure 4C:
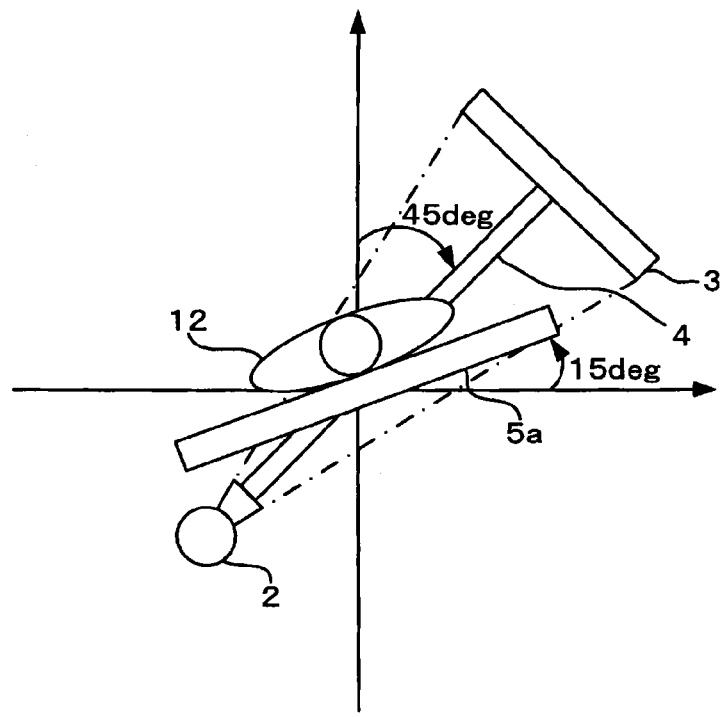
FIG. 4C is a diagram supplementing the descriptions of the flowchart according to the first embodiment.
Figure 4D:
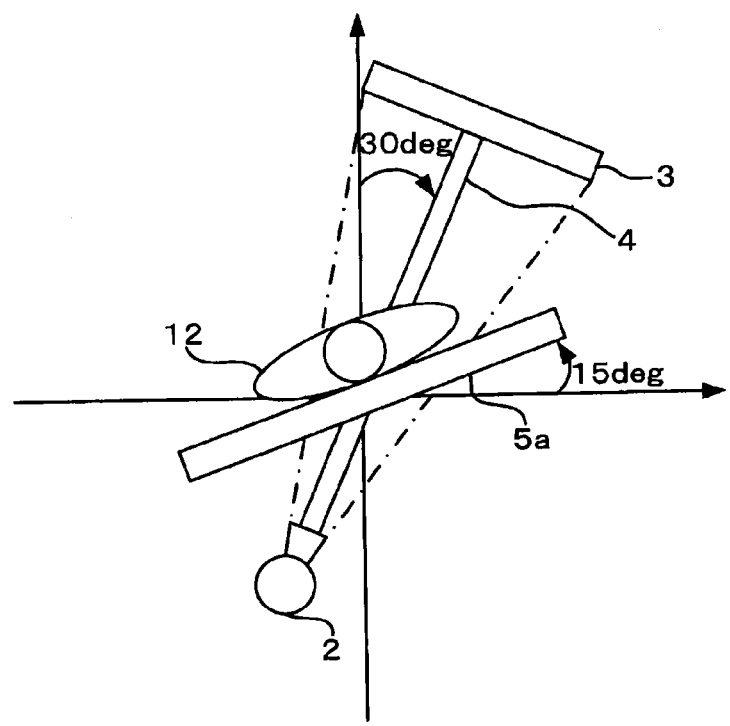
FIG. 4D is a diagram supplementing the descriptions of the flowchart according to the first embodiment.

Next, operations of the X-ray imaging system 1 according to the present embodiment will be described with reference to FIG. 3 through FIG. 4D. FIG. 4A through FIG. 4D are diagrams showing the subject 12 placed on the tabletop 5a as observed from the head direction (same as in FIG. 2B). Here, the state in which the support unit 4 (i.e., the X-ray generator 2 and the X-ray detector 3) is perpendicular to the lateral-direction axis of the tabletop 5a refers to state in which "the tilt of the support unit 4 is 0°" (refer to FIG. 4A). Moreover, the state in which the tabletop 5a is not tilted refers to state in which "the tilt of the tabletop 5a is 0°" (refer to FIG. 4A).

First, using the operating unit 10, the operator selects any item of information from among the multiple items of auto-positioning information. The calculator 9 reads out the selected auto-positioning information from the memory 8 (S10). In the present embodiment, the selected auto-positioning information (position information) includes the tilt angles of the support unit 4 and the tabletop 5a. In the present embodiment, the support unit 4 (i.e., the X-ray generator 2 and the X-ray detector 3) is tilted 45° in the RAO direction, and the tilt of the tabletop 5a is 0° (refer to FIG. 4B).

Next, the tilt detector 7 detects the current tilt angle of the tabletop 5a (S11). In the present embodiment, the tabletop 5a is tilted 15° in the LAO direction (lateral direction) (refer to FIG. 4C; there is no tilt in the longitudinal direction). Information indicating the detected tilt angle is sent to the calculator 9, as a result of the detection performed by the tilt detector 7.

Next, based on the auto-positioning information read out in S10 and the information indicating the current tilt angle of the tabletop 5a sent in S11, the calculator 9 calculates a correction angle that corrects the auto-positioning information (S12). In the present embodiment, the operator wishes to perform X-ray imaging with no tilt in the tabletop 5a and with the support unit 4 located at a position forming a 45° angle in the RAO direction. Consequently, if the support unit 4 is moved based on the auto-positioning information with the tabletop 5a tilted 15° in the LAO direction, the support unit 4 moves 60° in relation to the tabletop 5a. Therefore, based on the angle of the support unit 4 in relation to the tabletop 5a when the support unit 4 is actually moved based on the auto-positioning information (60° in the RAO direction) and on the value of the auto-positioning information (45° in the RAO direction), the calculator 9 calculates "−15° in the RAO direction" as the correction angle. The calculated correction angle is sent to the controller 11.

Next, based on the auto-positioning information selected in S10 and on the correction information calculated in S12, the controller 11 calculates angle to use to move the support unit 4 (S13). In the present embodiment, based on the information "45° in the RAO direction" and "−15° in the RAO direction", "30° in the RAO direction" is obtained as the angle to move the support unit 4.

Furthermore, the process of obtaining the angle in S13 may be executed by the calculator 9 or the drive unit 6. Alternatively, the X-ray imaging system 1 may be configured to include a movement-angle calculator (not shown) for obtaining the angle of S13.

Then, based on the control of the controller 11, the drive unit 6 moves the support unit 4 so as to form the angle obtained in S13 (S14; refer to FIG. 4D).

After the above operations are completed, based on an X-ray imaging instruction from the operating unit 10, X-ray imaging of the subject 12 is performed (S15).

<Operational Effects of the First Embodiment>

In the present embodiment, the X-ray imaging system 1 includes the support unit 4 that holds the X-ray imaging unit performing X-ray imaging of the subject 12. The subject 12 is placed on the tabletop 5. The memory 8 stores in advance imaging angle information at the time of past imaging. The tilt detector 7 detects the tilt angle of the tabletop 5a. The calculator 9 calculates a correction angle for correcting the imaging angle information based on the imaging angle information stored in the memory 8 and on the tilt angle detected by the tilt detector 7. Then, the drive unit 6 moves the support unit 4 to a position based on the imaging angle information and on the correction angle.

In other words, it is possible to adjust the relative positional relationship of the support unit 4 and the X-ray imaging unit while considering the tilt angle of the tabletop 5a. Consequently, it becomes possible to acquire X-ray images from a desired direction.

Moreover, in the present embodiment, as imaging angle information, position information (i.e., auto-positioning information) of the support unit 4 that is linked to arbitrary identifiers is used. Based on the position information and on the tilt angle detected by the tilt detector 7, the calculator 9 calculates the correction angle that corrects the position angle. Then, the drive unit 6 moves the support unit 4 to a position based on the position information and on the correction angle calculated by the calculator 9.

Consequently, when executing auto-positioning, it is possible to adjust the relative positional relationship of the support unit 4 and the X-ray imaging unit while considering the tilt angle of the tabletop 5a. In other words, it becomes possible to acquire X-ray images from a desired direction.

<Variation of the First Embodiment>

In the first embodiment, auto-positioning information is used as the imaging angle information, but the present invention is not limited to this. It is also possible to use, for example, auto-angle information.

Auto-angle information refers to supplementary information (imaging angle information) of medical images collected in the past. Examples of medical devices that collect medical images include X-ray CT devices.

An X-ray CT device is able to image a subject from various angles and reconstruct CT images (tomographic images and three-dimensional images) based on the imaging results.

Here, there are cases in which, as a result of observing, for example, a three-dimensional CT image from various viewing angles, the operator wishes to perform imaging by using the X-ray imaging system 1 from a specific angle.

In this variation, a configuration that is effective for such cases, that is, a configuration that is able to determine the angle of the support unit 4 of the X-ray imaging system 1 using information attached to CT images—will be described, with a focus on configurations different from the first embodiment.

<Device Configuration>

As in the first embodiment, the X-ray imaging system 1 according to the present variation includes the X-ray generator 2, the X-ray detector 3, the support unit 4, the couch 5, the drive unit 6, the tilt detector 7, the memory 8, the calculator 9, the operating unit 10, and the controller 11 (refer to FIG. 1).

In the present embodiment, the imaging angle information stored in the memory 8 is information attached to images imaged by another medical device (not shown). For example, in CT images imaged by an X-ray CT device, imaging angle information corresponding to the viewing angle is present as supplementary information. The memory 8 receives these items of supplementary information from the X-ray CT device together with the images and stores them.

<Operations of the X-Ray Imaging System 1>

Figure 5:
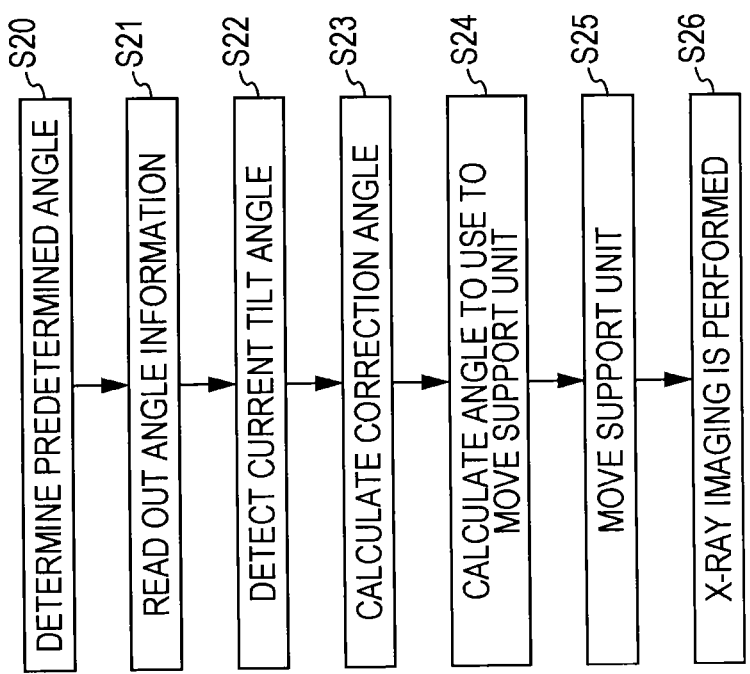
FIG. 5 is a flowchart showing an overview of processes performed by the X-ray imaging system according to a variation of the first embodiment.

Next, operations of the X-ray imaging system 1 according to the present variation will be described with reference to FIG. 5. In the present variation, the other medical device shall be described as being an X-ray CT device. Moreover, the definitions of the terms "CRA", "CAU", "LAO", "RAO" described in the first embodiment are also applicable to the tabletop of the X-ray CT device (i.e., the portion of the X-ray CT device where the subject is placed).

First, the operator observes a three-dimensional CT image imaged by the X-ray CT device in the display (not shown) of the X-ray imaging system 1, for example, and determines a predetermined angle for performing X-ray imaging (S20).

Next, using the operating unit 10, the operator issues an instruction to select an image corresponding to the angle determined in S20. Based on this selection, the calculator 9 reads out supplementary imaging angle information (auto-angle information) together with the corresponding image from the memory 8 (S21). In the present embodiment, as auto-angle information, a value indicating "30° in the CAU direction; tilt of the tabletop is 0°" is attached to the selected image.

Next, based on the input from the operating unit 10, the tilt detector 7 detects the current tilt angle of the tabletop 5a (S22). In the present embodiment, we shall suppose that as a result of the detection performed by the tilt detector 7, the tabletop 5a is tilted 10° in the CAU direction (we shall suppose that there is no tilt in the lateral direction). Information indicating the detected tilt angle is sent to the calculator 9.

Next, based on the auto-angle information read out in S21 and on the information indicating the current tilt angle of the tabletop 5a sent in S22, the calculator 9 calculates a correction angle for correcting the auto-angle information (S23). In the present embodiment, the operator wishes to perform X-ray imaging with no tilt in the tabletop 5a and to perform X-ray imaging at a position of the support unit 4 forming a 30° angle in the CAU direction. Consequently, when the support unit 4 is moved based on the auto-angle information with the tabletop 5a tilted 15° in the CAU direction, the support unit 4 is moved 15° in relation to the tabletop 5a. Therefore, based on the angle of the support unit 4 in relation to the tabletop 5a when the support unit 4 is actually moved based on the auto-angle information (15° in the CAU direction) and on the value of the auto-angle information (30° in the CAU direction), the calculator calculates "15° in the CAU direction" as the correction angle. The calculated correction angle is sent to the controller 11.

Next, based on the auto-angle information selected in S21 and the correction information calculated in S23, the controller 11 calculates the angle to use to move the support unit 4 (S24). In the present embodiment, based on the items of information "30° in the CAU direction" and "15° in the CAU direction", "15° in the CAU direction" is obtained as the angle to use to move the support unit 4.

Furthermore, the process of obtaining the angle of S24 may be executed by the calculator 9 or the drive unit 6. Alternatively, the X-ray imaging system 1 may be configured to include a movement-angle calculator (not shown) for obtaining the angle of S24.

Then, based on the control of the controller 11, the drive unit 6 moves the support unit 4 so as to form the angle obtained in S24 (S25).

After the completion of the above operations, based on an X-ray imaging instruction from the operating unit 10, X-ray imaging of the subject 12 is performed (S26).

<Operational Effects of the Variation of the First Embodiment>

In the present embodiment, supplementary information of images imaged by another medical device is used as the imaging angle information. Based on the supplementary information and on the tilt angle detected by the tilt detector 7, the calculator 9 calculates the correction angle for correcting the supplementary information. Then, the drive unit 6 moves the support unit 4 to a position based on the supplementary information and on the correction angle calculated by the calculator 9.

In other words, even when auto-angle is executed, it is possible to adjust the angle of the support unit 4 in consideration of the tilt angle of the tabletop 5a. Consequently, it is possible to acquire X-ray images from a desired direction.

Second Embodiment

Next, using FIG. 6 and FIG. 7, the configuration of the X-ray imaging system 1 according to the second embodiment will be described. Configurations identical to those of the first embodiment will be described only briefly.

For example, in manipulations to improve states of vascular occlusion, there are cases in which X-ray imaging is performed before and after the manipulation to confirm whether the blockage of the blood vessels has improved by comparing the obtained X-ray imaging images. The pre-manipulation X-ray imaging images referenced in such a case (hereinafter also referred to as "past images" in the present embodiment) are preferably X-ray imaging images obtained using the same arrangement as that of the current (i.e., when performing post-manipulation X-ray imaging) relative positions of the support unit 4 and the tabletop 5a.

In the present embodiment, a configuration will be described in which past images are acquired in consideration of the tilt of the tabletop 5a.

<Device Configuration>

Figure 6:
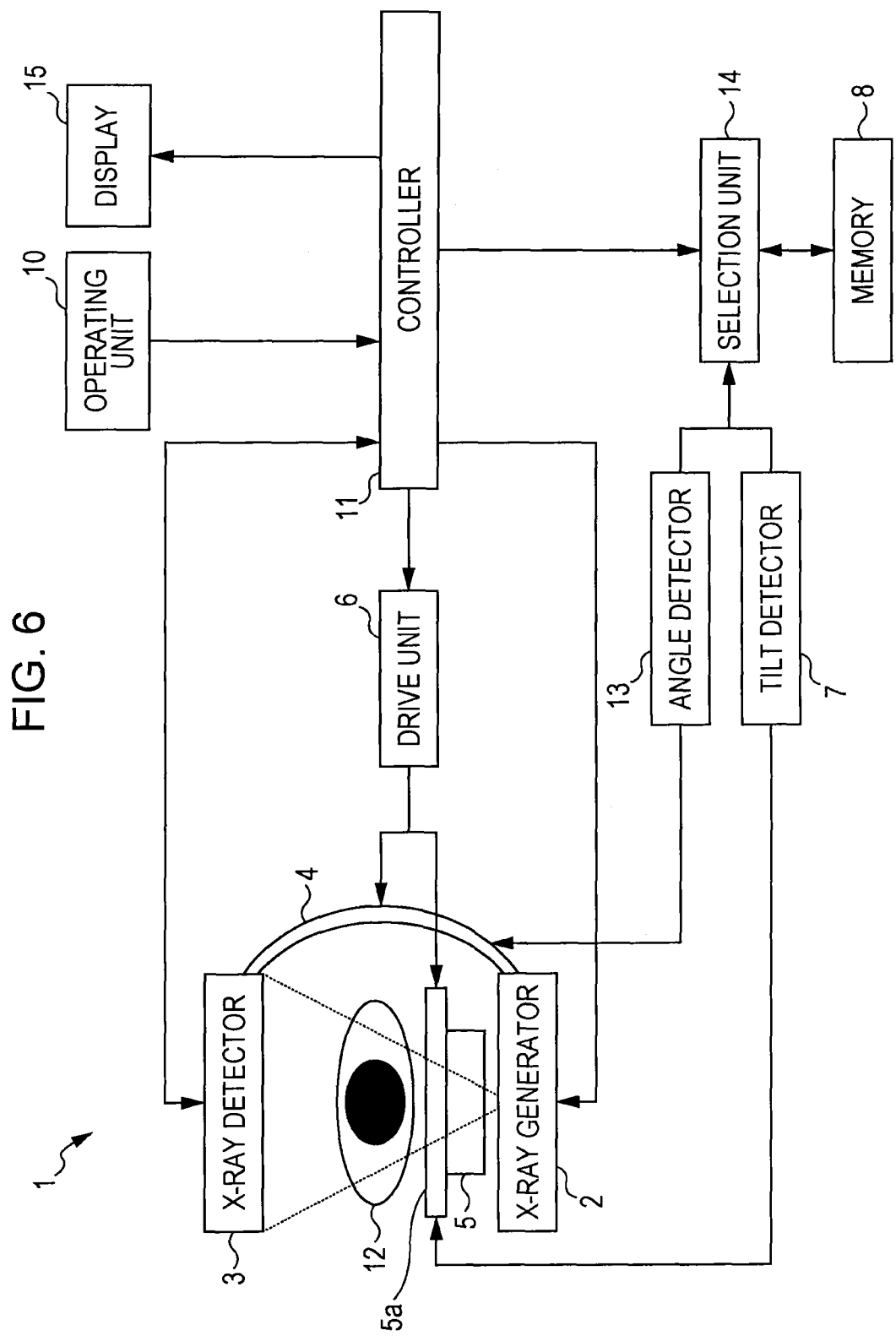
FIG. 6 is a block diagram showing the configuration of the X-ray imaging system according to the second embodiment.
Figure 7:
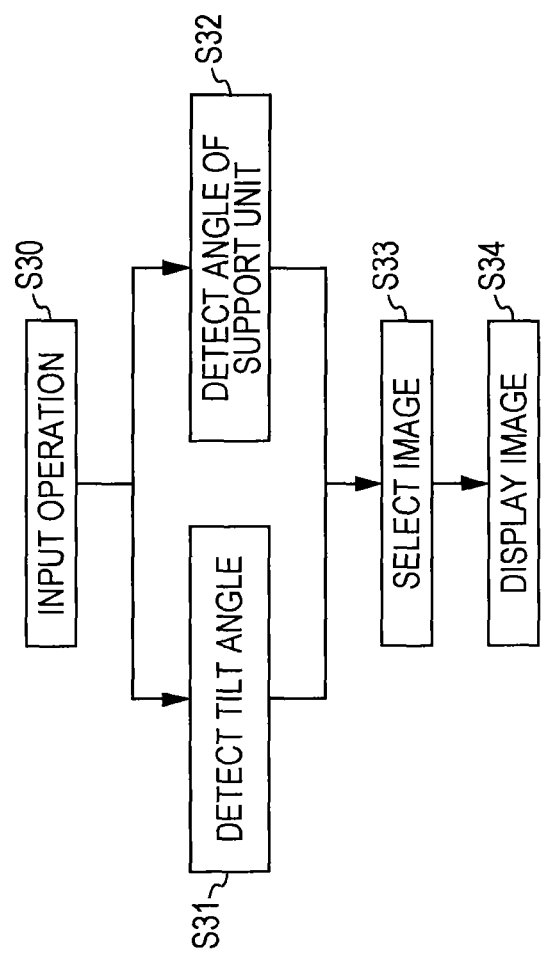
FIG. 7 is a flowchart showing an overview of processes performed by the X-ray imaging system according to the second embodiment.

As shown in FIG. 6, the X-ray imaging system 1 includes the X-ray generator 2, the X-ray detector 3, the support unit 4, the couch 5, the drive unit 6, the tilt detector 7, the memory 8, the operating unit 10, the controller 11, the angle detector 13, the selection unit 14, and the display 15. During X-ray imaging, the subject 12 is arranged between the X-ray generator 2 and the X-ray detector 3.

The X-ray generator 2 has a function to generate X-rays and irradiate the X-rays to the region of the subject 12 being examined. The X-ray detector 3 has a function to detect X-rays that have been irradiated from the X-ray generator 2 to the subject 12 and have transmitted the subject 12. The support unit 4 holds the X-ray generator 2 and the X-ray detector 3. In the present embodiment, the X-ray generator 2 and the X-ray detector 3 configure the "X-ray imaging unit". In other words, it may be be that the support unit 4 holds the X-ray imaging unit. The couch 5 includes the movable tabletop 5a. The subject 12 that is the subject of X-ray imaging is placed on the tabletop 5a. Moreover, the tabletop 5a is moved and tilted by the drive unit 6. The drive unit 6 has a function to drive the support unit 4 and the tabletop 5a. The tilt detector 7 has a function to detect the tilt angle of the tabletop 5a. The operating unit 10 is used to input the details of various operations of the X-ray imaging system 1. The controller 11 has a function to control the operations of each configuration of the X-ray imaging system 1.

The memory 8 has a function to store multiple X-ray imaging images (past images) from the X-ray imaging unit. Furthermore, information related to the angle of the support unit 4 during imaging as well as the tilt angle of the tabletop 5a (i.e., imaging angle information) are linked to the X-ray imaging images as supplementary information.

The angle detector 13 has a function to detect the angle of the support unit 4 in relation to the tabletop 5a. Based on an instruction from the operating unit 10 to detect the angle, the angle detector 13 detects the angle of the support unit 4 at that point in time. Angle detection is performed by, for example, providing angle sensors (not shown) on both the support unit 4 and the tabletop 5a and detecting the angle of the support unit 4 in relation to the tabletop 5a based on the detection results of each angle sensor. Alternatively, it is also possible to perform angle detection based on control information from the controller 11.

In the present embodiment, the tilt detector 7 and the angle detector 13 are described as separate configurations, but the present invention is not limited to this. For example, it is possible to detect both the angle of the support unit 4 and the tilt angle of the tabletop 5a using the angle detector 13.

The selection unit 14 has a function to select an X-ray imaging image stored in the memory 8 based on the angle detected by the angle detector 13 and on the tilt angle detected by the tilt detector 7. Specifically, the selection unit 14 obtains an angle that couples the angle of the support unit 4 detected by the angle detector 13 with the tilt angle of the tabletop 5a. Then, the selection unit 14 performs a process to select an X-ray imaging image that includes imaging angle information equivalent (or nearest) to that angle as supplementary information from the memory 8.

If there is no X-ray imaging image including imaging angle information equivalent to the angle obtained by the selection unit 14, it is possible to display a warning display on the display 15, etc. indicating that there is no X-ray imaging image including equivalent imaging angle information.

The display 15 has a function to display the X-ray imaging image selected by the selection unit 14. The display 15 is composed of a display device such as, for example, a monitor. Moreover, in the present embodiment, the display 15 is described as part of the X-ray imaging system 1, but the present invention is not limited to this. For example, it is also possible to display X-ray images, etc. on the monitor of a computer provided separately from the X-ray imaging system 1.

<Operations of the X-Ray Imaging System 1>

Next, operations of the X-ray imaging system 1 according to the present embodiment will be described with reference to FIG. 7. Here, a case will be described in which one wishes to confirm X-ray imaging images obtained in the past with the support unit 4 and the tabletop 5a located in a specific positional relationship.

First, using the operating unit 10, the operator inputs an operation to read out an X-ray imaging image obtained in a specific positional relationship (S30).

Based on the operational input in S30, the tilt detector 7 detects the current tilt angle of the tabletop 5a (S31). In the present embodiment, we shall suppose that as a result of the detection by the tilt detector 7, the tabletop 5a is tilted 10° in the CRA direction (we shall suppose that there is no tilt in the lateral direction). Information indicating the detected tilt angle is sent to the selection unit 14.

Moreover, based on the operational input in S30, the angle detector 13 detects the angle of the support unit 4 in relation to the tabletop 5a (S32). In the present embodiment, we shall suppose that as a result of the detection by the angle detector 13, the support unit 4 is tilted 30° in the RAO direction in relation to the tabletop 5a. Information indicating the detected angle of the support unit 4 is sent to the selection unit 14.

It is not necessary for the steps of S31 and S32 to be executed simultaneously. For example, the processes of S32 may be performed after the completion of the processes of S31.

Next, based on the tilt angle of the tabletop 5a sent in S31 and on the angle of the support unit 4 in relation to the tabletop 5a sent in s32, the selection unit 14 performs a process of selecting an X-ray imaging image (S33). In the present embodiment, the tabletop 5a is tilted 10° in the CRA direction, and the support unit 4 is tilted 30° in the RAO direction in relation to the tabletop 5a. In other words, it may be that past X-ray imaging images corresponding to the current specific positional relationship are those that were imaged under the conditions of 10° in the CRA direction and 30° in the RAO direction. Consequently, the selection unit 14 selects a past image including these conditions as supplementary information from the memory 8 and sends it to the display 15.

If none of the items of supplementary information of the X-ray imaging images stored in the memory 8 match the conditions, it is possible for the selection unit 14 to select an X-ray imaging image including supplementary information that is closest to those conditions and send it to the display 15.

As can be seen above, an X-ray imaging image selected by the selection unit 14 is displayed on the display 15 (S34).

<Operational Effects of the Second Embodiment>

In the present embodiment, the X-ray imaging system 1 includes the support unit 4 that holds the X-ray imaging unit performing X-ray imaging of the subject 12. The subject 12 is placed on the tabletop 5a. The memory 8 stores multiple X-ray imaging images of the subject 12 captured by the X-ray imaging unit. The tilt detector 7 detects the tilt angle of the tabletop 5a. The angle detector 13 detects the angle of the support unit 4 in relation to the tabletop 5a. Based on the angle detected by the angle detector 13 and on the tilt angle detected by the tilt detector 7, the selection unit 14 selects an X-ray imaging image stored in the memory 8. Then, the display 15 displays the X-ray imaging image selected by the selection unit 14.

In other words, when selecting an X-ray imaging image obtained in the past with the support unit 4 and the tabletop 5a located in a specific positional relationship, it is possible to select considering the current tilt angle of the tabletop 5a. Consequently, it is possible to display a past image corresponding to the current specific positional relationship.

Third Embodiment

The configuration of the X-ray imaging system 1 according to the third embodiment will be described with reference to FIG. 8 and FIG. 9. Configurations identical to those of the first embodiment will be described only briefly.

Due to the structure of the X-ray imaging system 1, the range of movement (i.e., the maximum angle of movement; hereinafter also referred to as the "stroke limit") of the support unit 4 is determined in advance.

Consequently, as described in the first embodiment, for example, when moving the support unit 4 by incorporating the tilt angle of the tabletop 5a, depending on the positional relationship of the tabletop 5a and the support unit 4, the movement of the support unit 4 may be limited by the stroke limit. For example, if the angle for moving the support unit 4 based on the value calculated by the calculator 9 is 60° in the LAO direction when the support unit 4 has a stroke limit of 50° in the LAO direction, the support unit 4 is unable to move beyond 50° in the LAO direction.

In the present embodiment, a configuration used in such cases in which movement of the support unit 4 exceeding the stroke limit is required is described.

<Device Configuration>

Figure 8:
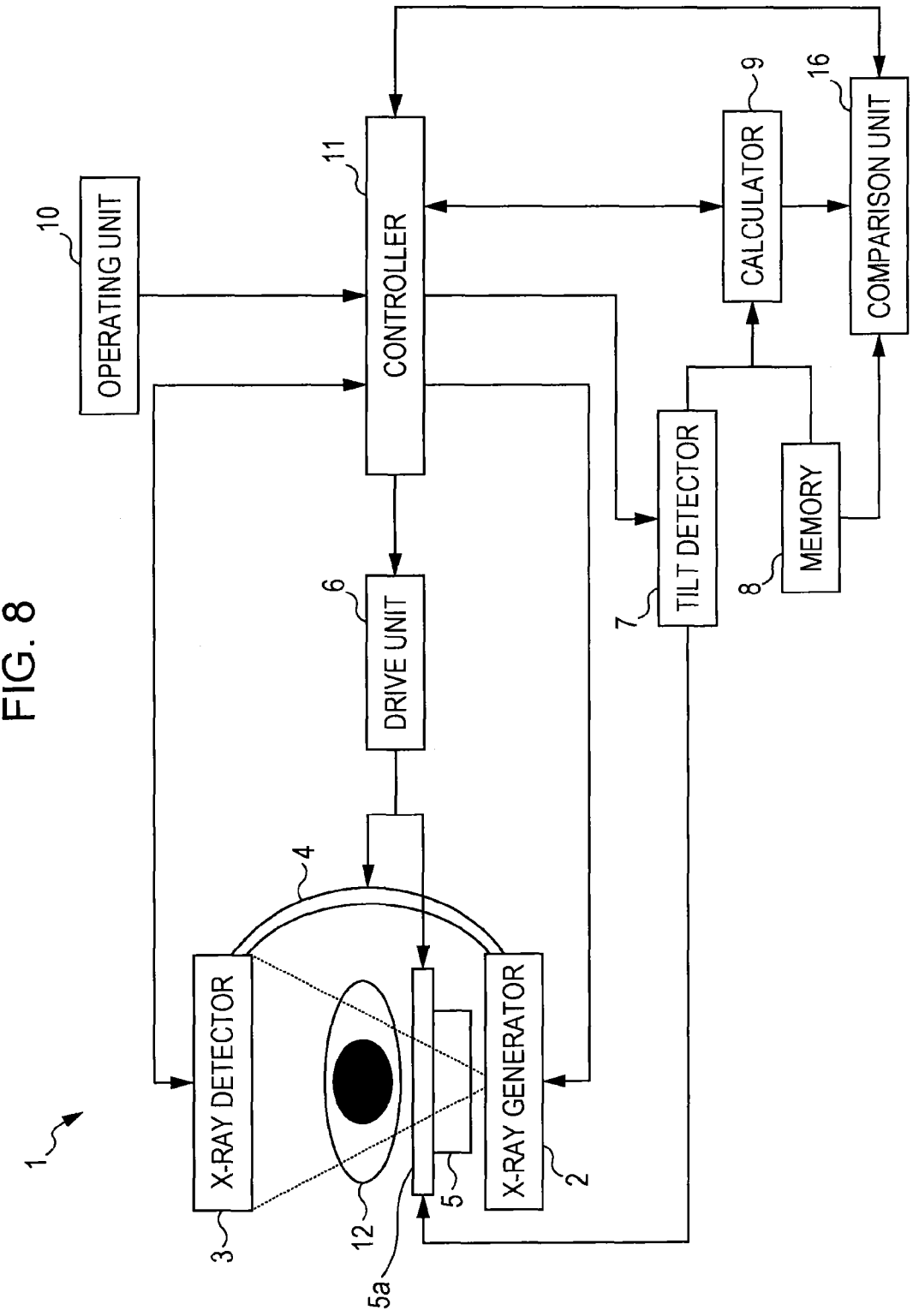
FIG. 8 is a block diagram showing the configuration of the X-ray imaging system according to the third embodiment.
Figure 9:
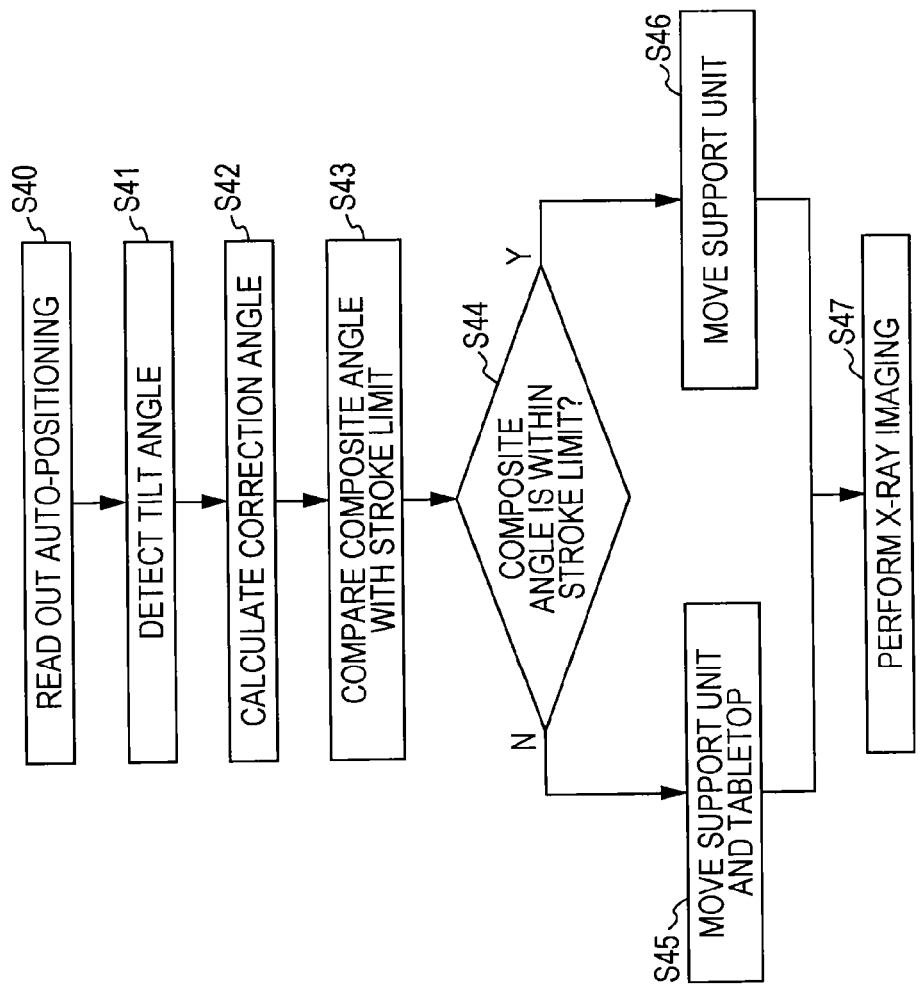
FIG. 9 is a flowchart showing an overview of processes performed by the X-ray imaging system according to the third embodiment.

As shown in FIG. 8, the X-ray imaging system 1 includes the X-ray generator 2, the X-ray detector 3, the support unit 4, the couch 5, the drive unit 6, the tilt detector 7, the memory 8, the calculator 9, the operating unit 10, the controller 11, and the comparison unit 16.

The X-ray generator 2 has a function to generate X-rays and irradiate the X-rays to the region of the subject 12 being examined. The X-ray detector 3 has a function to detect X-rays that have been irradiated from the X-ray generator 2 to the subject 12 and have transmitted the subject 12. The support unit 4 holds the X-ray generator 2 and the X-ray detector 3. In the present embodiment, the X-ray generator 2 and the X-ray detector 3 configure the "X-ray imaging unit". In other words, the support unit 4 holds the X-ray imaging unit. The couch 5 includes the movable tabletop 5a. The subject 12 that is subject to X-ray imaging is placed on the tabletop 5a. Moreover, the tabletop 5a is moved and tilted by the drive unit 6. The drive unit 6 has a function to drive the support unit 4 and the tabletop 5a. The tilt detector 7 has a function to detect the tilt angle of the tabletop 5a. The memory 8 has a function to store imaging angle information as well as detection results, etc. from the X-ray detector 2. The calculator 9 has a function to calculate a correction angle that corrects imaging angle information based on imaging angle information (information indicating the angle of the support unit 4, and the tilt angle detected by the tilt detector 7) stored in the memory 8.

The operating unit 10 is used to input the details of various operations of the X-ray imaging system 1.

The comparison unit 16 has a function to compare the composite angle obtained based on the imaging angle information and the correction angle calculated by the calculator 9 with the range of movement of the support unit 4.

Specifically, the comparison unit 16 calculates the composite angle by performing an addition process of the imaging angle information stored in the memory 8 and the correction angle calculated by the calculator 9. Then, the comparison unit 16 compares the composite angle with the range of movement (stroke limit) of the support unit 4. When it determines that the composite angle exceeds the range of movement, the comparison unit 16 calculates the difference (i.e., the difference between the range of movement and the composite angle) and sends the results to the controller 11. Moreover, when it determines that the composite angle does not exceed the range of movement, the comparison unit 16 sends the results to the controller 11.

When the comparison unit 16 determines that the composite angle does not exceed the range of movement, the controller 11 performs operational control of the drive unit 6 so as to cause it to move the support unit 4 to a position based on the imaging angle information and the correction angle calculated by the calculator 9.

On the other hand, when the comparison unit 16 determines that the composite angle exceeds the range of movement, the controller 11 moves the support unit 4 and, based on the difference sent from the comparison unit 16, also performs operational control of the drive unit 6 to cause it to move the tabletop 5a.

<Operations of the X-Ray Imaging System 1>

Next, operations of the X-ray imaging system 1 according to the present embodiment will be described with reference to FIG. 9. In the present embodiment, we shall suppose that the stroke limit in the LAO direction of the support unit 4 is 50°.

First, using the operating unit 10, from among the multiple items of auto-positioning information, the operator selects information on the position of the support unit 4 at which X-ray imaging is to be performed. The controller 11 reads out the corresponding auto-positioning information from the memory 8 based on the selection and sends it to the calculator 9 (S40). In the present embodiment, the selected auto-positioning information includes the tilt angles of the support unit 4 and the tabletop 5a. In the present embodiment, we shall suppose that the support unit 4 is tilted 45° in the LAO direction and that the tabletop 5a has a tilt of 0°.

Next, based on an input from the operating unit 10, the tilt detector 7 detects the current tilt angle of the tabletop 5a (S41). In the present embodiment, we shall suppose that as a result of the detection by the tilt detector 7, the tabletop 5a is tilted 15° in the LAO direction (lateral direction) (we shall suppose that there is no tilt in the longitudinal direction). Information indicating the detected tilt angle is sent to the calculator 9.

Next, based on the auto-positioning information sent in S40 and the information indicating the current tilt angle of the tabletop 5a sent in S41, the calculator 9 calculates a correction angle that corrects the auto-positioning information (S42). In the present embodiment, the operator wishes to perform X-ray imaging with no tilt in the tabletop 5a and with the support unit 4 located at a position forming a 45° in the LAO direction. Consequently, when the support unit 4 is moved based on the auto-positioning information with the tabletop 5a tilted 15° in the LAO direction, the support unit 4 moves 30° in the LAO direction in relation to the tabletop 5a. Therefore, based on the angle (30° in the LAO direction) of the support unit 4 in relation to the tabletop 5a when the support unit 4 is actually moved and on the value of the auto-positioning information (45° in the LAO direction), the calculator 9 calculates "15° in the LAO direction" as the correction angle. The calculated correction angle is sent to the controller 11.

Next, the comparison unit 16 calculates a composite angle based on the correction angle obtained in S42 and the imaging angle information stored in the memory 8. Then, the comparison unit 16 compares the composite angle with the stroke limit of the support unit 4 (S43). In the present embodiment, the composite angle is the total of the 15° in the LAO direction obtained in S42 and the 45° in the LAO direction that is the imaging angle information, that is 60°. In other words, when the support unit 4 is moved based on the composite angle, the support unit 4 is tilted 60° in the LAO direction.

The stroke limit in the present embodiment is only 50° in the LAO direction. In other words, in this case, it is impossible to move the support unit 4 (S44: N). Consequently, the comparison unit 16 calculates the difference between the range of movement and the composite angle (−10° in the LAO direction) and sends the results to the controller 11.

When the result in S44 is N, the controller 11 performs control to move the tabletop 5 based on only the information indicating the angle difference sent from the comparison unit 16 (−10° in the LAO direction). Based on this control, the drive unit 6 tilts the support unit 4 by 50° in the LAO direction and also tilts the tabletop 5a by −10° in the LAO direction (S45). As a result, the support unit 4 and the tabletop 5a have a relative tilt of 60°.

On the other hand, when the result in S44 is Y, based on the control of the controller 11, the drive unit 6 moves only the support unit 4 (S46).

After the completion of the above operations, based on an X-ray imaging instruction from the operating unit 10, X-ray imaging of the subject 12 is performed (S47).

<Operational Effects of the Third Embodiment>

In the present embodiment, the X-ray imaging system 1 includes the support unit 4 that holds the X-ray imaging unit performing X-ray imaging of the subject 12. The subject 12 is placed on the tabletop 5a. The memory 8 stores in advance imaging angle information from past imaging. The tilt detector 7 detects the tilt angle of the tabletop 5a. Based on the imaging angle information stored in the memory 8 and on the tilt angle detected by the tilt detector 7, the calculator 9 calculates a correction angle to correct the imaging angle information. The comparison unit 16 compares a composite angle obtained based on the imaging angle information and the correction angle with the range of movement of the support unit 4. Then, when the comparison unit 16 determines that the composite angle exceeds the range of movement, the drive unit 6 moves at least one of the tabletop 5a and the support unit 4 so that the tabletop 5a and the support unit 4 form the composite angle.

In other words, as a result of adjusting the angle of the support unit 4 while considering the tilt angle of the tabletop 5a, even if the result exceeds the stroke limit of the support unit 4, it becomes possible to realize angle adjustment by moving the tabletop 5a. Consequently, it becomes possible to acquire X-ray images from a desired direction.

In the present embodiment, a configuration using auto-positioning information has been described, but the present invention is not limited to this. For example, even with a configuration using auto-angle information, it is also possible to perform angle adjustments based on considerations of the stroke limit of the support unit 4.

Moreover, in the present embodiment, a configuration that moves the support unit up to the stroke limit and moves the tabletop 5a by only the missing angle has been described, but the present invention is not limited to this. For example, in the abovementioned S45, the support unit 4 may be tilted by 40° in the LAO direction while tilting the tabletop 5a by −20° in the LAO direction.

Fourth Embodiment

A configuration of the X-ray imaging system 1 according to the fourth embodiment will be described with reference to FIG. 10 and FIG. 11. Configurations identical to those of the first embodiment will be described only briefly.

X-ray imaging systems include so-called Bi-place systems that enable imaging of a single subject from two directions at once.

Generally, a Bi-plane system includes a dual imaging system composed of a first imaging system that images a subject from the anterior direction and a second imaging system that images the subject from a lateral direction while the subject is placed on their back on the tabletop.

In this type of second imaging system, an FPD (Flat Panel Detector) is used as an X-ray detector. Generally, in this FPD, a predetermined direction of the frame and the longitudinal direction of the tabletop are arranged in a parallel relationship (in the present embodiment, the direction of one side of the frame of the FPD and the longitudinal direction of the tabletop of the X-ray imaging system are arranged in a parallel state). Consequently, when the tabletop is tilted, the position of the subject placed on the tabletop in relation to the FPD changes. In other words, a misalignment is generated in the X-ray imaging images obtained by the second imaging system.

In the present embodiment, a configuration allowing X-ray imaging to be performed by taking into consideration the tilt of the tabletop in a Bi-plane system is described.

<Device Configuration>

Figure 10:
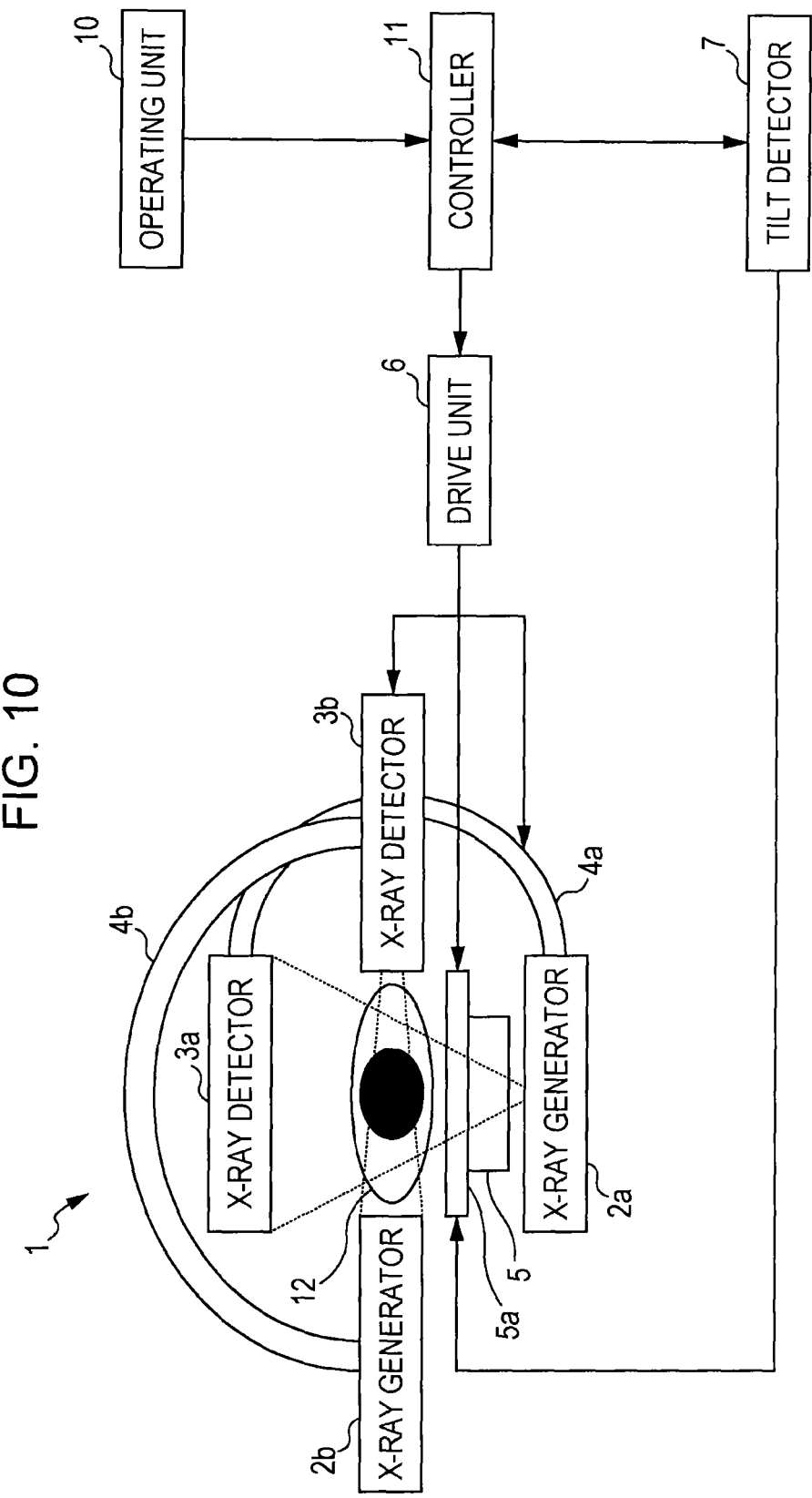
FIG. 10 is a block diagram showing the configuration of the X-ray imaging system according to the fourth embodiment.
Figure 11:
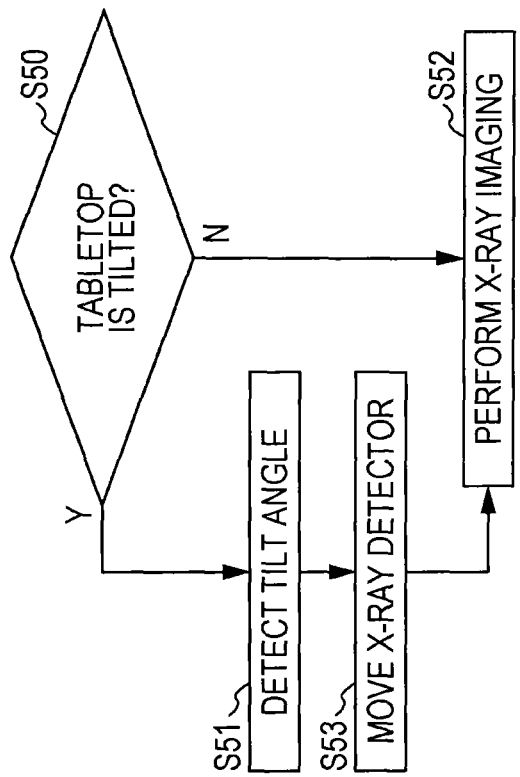
FIG. 11 is a flowchart showing an overview of processes performed by the X-ray imaging system according to the fourth embodiment.

As shown in FIG. 10, the X-ray imaging system 1 includes X-ray generators 2a, 2b, X-ray detectors 3a, 3b, support units 4a, 4b, the couch 5, the drive unit 6, the tilt detector 7, the operating unit 10, and the controller 11. During X-ray imaging, the subject 12 is arranged between the X-ray generator 2 and the X-ray detector 3.

The X-ray generator 2a generates X-rays and irradiates the region of the subject 12 being examined with X-rays from the dorsal direction (the lower direction of the subject 12 in FIG. 10). Moreover, the X-ray generator 2b generates X-rays and irradiates the region of the subject 12 being examined with X-rays from a lateral direction (the side direction of the subject 12 in FIG. 10). The X-ray generators 2a, 2b each include X-ray tubes (not shown) that generate X-rays.

The X-ray detector 3a has a function to detect X-rays that have been irradiated from the X-ray generator 2a to the subject 12 and that have transmitted the subject 12. Moreover, the X-ray detector 3b has a function to detect X-rays that have been irradiated from the X-ray generator 2b to the subject 12 and that have transmitted the subject 12. X-rays detected by the X-ray detectors 3a, 3b are converted into X-ray imaging information in, for example, the X-ray detectors 3a, 3b. Then, the X-ray image information is transmitted to and stored in the memory 8 via wiring, etc. that is not shown.

The support unit 4a holds the X-ray generator 2a and the X-ray detector 3a. Moreover, the support unit 4b holds the X-ray generator 2b and the X-ray detector 3b. The support units 4a, 4b have, for example, a shape like the letter C that is known as a C-arm. Moreover, in the present embodiment, the support unit 4b is fixed to the ceiling of the examination room, etc. in which the X-ray imaging system 1 is arranged. The support unit 4a is able to move in the vicinity of the couch 5 due to the drive unit 6. Moreover, the X-ray detector 3b held by the support unit 4b is able to rotate due to the drive unit 6. The X-ray generator 2a and the X-ray detector 3a are provided in mutually facing positions due to being held by the support unit 4a. Moreover, the X-ray generator 2b and the X-ray detector 3b are provided in mutually facing positions due to being held by the support unit 4b.

In the present embodiment, the X-ray generator 2a and the X-ray detector 3a configure the "first imaging system". Moreover, the X-ray generator 2b and the X-ray detector 3b configure the "second imaging system". Moreover, the first imaging system and the second imaging system together configure the "X-ray imaging unit". Moreover, the support unit 4a and the support unit 4b together configure the "support unit".

The couch 5 includes the movable tabletop 5a. The subject 12 that is subject to X-ray imaging is placed on the tabletop 5a. Moreover, the tabletop 5a is moved and tilted by the drive unit 6.

The drive unit 6 has a function to drive the support units 4a, 4b, the X-ray detector 3b, and the tabletop 5a. The drive unit 6 is able to drive the support units 4a, 4b, the X-ray detector 3b, and the tabletop 5a separately. In other words, the drive unit 6 is able to simultaneously drive the support units 4a, 4b, the X-ray detector 3b, and the tabletop 5a, and is also able to drive only one (or only two) of any of the support units 4a, 4b, the X-ray detector 3b, and the tabletop 5a.

The tilt detector 7 has a function to detect the tilt angle of the tabletop 5a. The operating unit 10 is used to input the details of various operations of the X-ray imaging system 1.

The controller 11 has a function to control the operations of various configurations of the X-ray imaging system 1, such as the X-ray generator 2, the X-ray detector 3, the drive unit 6, and the tilt detector 7. It should be noted that in FIG. 9, wiring from the controller 11 to the X-ray generators 2a, 2b and the X-ray detectors 3a, 3b has been omitted.

<Operations of the X-Ray Imaging System 1>

Next, operations of the X-ray imaging system 1 according to the present embodiment will be described with reference to FIG. 11.

When performing X-ray imaging using the second imaging system, the operator uses the operating unit 10 to issue an instruction for tilt detection to the tilt detector 7. Based on this instruction, the tilt detector 7 detects whether or not the tabletop 5 is currently tilted (S50).

When the tabletop 5a is not tilted (S50: N), tilt angle detection by the tilt detector 7 is not performed. In other words, the tabletop 5a is not tilted in relation to the second imaging system. In this case, based on the X-ray imaging instruction in the second imaging system from the controller 11, X-ray imaging of the subject 12 is started (S52).

On the other hand, when the tabletop 5a is tilted (S50: Y), the tilt detector 7 detects the tilt angle of the tabletop 5a (S51). In the present embodiment, we shall suppose that the tabletop 5a is tilted by 10° in the CAU direction.

Next, the controller 11 performs operational control of the drive unit 6 to cause it to move the X-ray detector 3b of the second imaging system proportionally to the tilt angle detected in S51 (S53). In the present embodiment, the drive unit 6 tilts the X-ray detector 3b by 10° in the CAU direction to make it parallel with the tabletop 5a.

After the completion of the above operations, based on an X-ray imaging instruction from the operating unit 10, X-ray imaging of the subject 12 is performed (S52).

<Operational Effects of the Fourth Embodiment>

In the present embodiment, the X-ray imaging system 1 includes the support units 4a, 4b that hold the X-ray imaging unit performing X-ray imaging of the subject 12. The subject 12 is placed on the tabletop 5a. The tilt detector 7 detects the tilt angle of the tabletop 5a. Then, the drive unit 6 moves the X-ray detector 3b by the tilt angle detected by the tilt detector 7.

In other words, it is possible to adjust the angle of the X-ray detector 3b by considering the tilt angle of the tabletop 5a. Consequently, it becomes possible to acquire X-ray images from a desired direction.

<Variation of the Fourth Embodiment>

In the fourth embodiment, cases in which, based on the detection results of the tilt detector 7, the X-ray detector 3b is the only configuration moved by the drive unit 6 have been described, but the present invention is not limited to this. For example, it is also possible to move the support unit 4b in addition to the X-ray detector 3b.

Furthermore, it is also possible to not only move the second imaging system but also to move it together with the first imaging system. For the movement of the first imaging, the configuration of the first embodiment, for example, is used.

<Others>

Several embodiments of the present invention have been described, but these embodiments have been presented as examples and are not intended to limit the scope of the invention. These new embodiments may be implemented in various other modes, and various omissions, substitutions, and changes may be made without deviating from the spirit of the invention. These embodiments and variations thereof are included in the scope and spirit of the invention, and are also included in the scope equivalent to the invention described in the scope of patent claims.

EXPLANATION OF SYMBOLS

1 X-ray imaging system
2 X-ray generator
3 X-ray detector
4 Support unit
5 Couch
5a Tabletop
6 Drive unit
7 Tilt detector
8 Memory
9 Calculator
10 Operating unit
11 Controller
12 Subject

What is claimed is:

1. An X-ray imaging system comprising:
   a support unit that holds an X-ray imaging unit that performs X-ray imaging for a subject;
   a tabletop on which the subject is placed;
   a memory configured to store in advance imaging angle information from past imaging, the imaging angle information being supplementary information of an image captured in a past by another medical device;
   a tilt detector configured to detects the tilt angle of the tabletop;
   a calculator configured to calculate a correction angle for correcting the imaging angle information based on the imaging angle information and the tilt angle; and
   a drive unit configured to move the support unit to a position based on the imaging angle information and the correction angle.

2. The X-ray imaging system according to claim 1, wherein the imaging angle information is position information of the support unit in past imaging, the information linked to an arbitrary identifier,
   the X-ray imaging system comprises an operating unit that performs operations to select a predetermined identifier from a plurality of the identifiers,
   the calculator calculates the correction angle for correcting the position information based on the position information that has been selected by the operating unit and is linked to the identifier, as well as on the tilt angle, and
   the drive unit moves the support unit to a position based on the position information and the correction angle.

3. An X-ray imaging system comprising:
   a support unit configured to holds an X-ray imaging unit that performs X-ray imaging of a subject;
   a tabletop on which the subject is placed;
   a memory configured to store an X-ray imaging image in association with imaging angle information including an angle of the support unit in relation to the tabletop and a tilt angle of the tabletop from past imaging, the imaging angle information being supplementary information of the X-ray imaging image captured in a past by another medical device;
   a tilt detector configured to detect the tilt angle of the tabletop;
   an angle detector configured to detect the angle of the support unit in relation to the tabletop;
   a selection unit configured to select an X-ray imaging image stored in the memory in association with the imaging angle information including same angles as the angle detected by the angle detector and the tilt angle detected by the tilt detector; and
   a display configured to display the selected X-ray imaging image.

4. The X-ray imaging system according to claim 1, further comprising:
   a comparison unit configured to compares a composite angle obtained based on the imaging angle information and the correction angle with the range of movement of the support unit, wherein
   when the comparison unit determines that the composite angle exceeds the range of movement, the drive unit moves at least one of either the tabletop or the support unit so that the tabletop and the support unit form the composite angle.

5. An X-ray imaging system comprising:
   a support unit configured to hold an X-ray imaging unit that performs X-ray imaging of a subject;
   a tabletop on which the subject is placed;
   a memory configured to store in advance imaging angle information from past imaging, the imaging angle information being supplementary information of an image captured by another medical device;
   a tilt detector configured to detect the tilt angle of the tabletop;
   a calculator configured to calculate a correction angle for correcting the imaging angle information based on the imaging angle information and the tilt angle;
   a comparison unit configured to compare a composite angle obtained based on the imaging angle information and the correction angle with the range of movement of the support unit; and
   a drive unit that, when the comparison unit determines that the composite angle exceeds the range of movement of the support unit, moves at least one of either the tabletop or the support unit so that the tabletop and the support unit form the composite angle.

* * * * *